US007022341B2

(12) United States Patent
Abelaira et al.

(10) Patent No.: US 7,022,341 B2
(45) Date of Patent: Apr. 4, 2006

(54) PHARMACEUTICAL COMPOSITIONS CONTAINING EPINASTINE AND PSEUDOEPHEDRINE

(75) Inventors: Sara Abelaira, Buenos Aires (AR); Daniel Bianchi, Buenos Aires (AR); Francisco Gel, Buenos Aires (AR); Victor Denker, Buenos Aires (AR); Mabel Fernandez, Buenos Aires (AR); Marta Cicconi de Vidal, Buenos Aires (AR)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 10/448,568

(22) Filed: May 29, 2003

(65) Prior Publication Data

US 2003/0203021 A1    Oct. 30, 2003

Related U.S. Application Data

(63) Continuation of application No. 09/971,870, filed on Oct. 5, 2001, now abandoned.

(60) Provisional application No. 60/252,761, filed on Nov. 22, 2000.

(30) Foreign Application Priority Data

Oct. 6, 2000    (EP)    .................. 00121828

(51) Int. Cl.
*A61K 9/24* (2006.01)
*A61K 9/20* (2006.01)
*A61K 9/22* (2006.01)
*A61K 9/28* (2006.01)

(52) U.S. Cl. ............ 424/472; 424/464; 424/465; 424/468; 424/474

(58) Field of Classification Search ........ 424/464, 424/465, 468, 474, 472
See application file for complete search history.

(56) References Cited

U.S. PATENT DOCUMENTS

| 4,996,061 | A |   | 2/1991 | Webb et al. |
| 5,314,697 | A |   | 5/1994 | Kwan et al. |
| 5,681,582 | A |   | 10/1997 | Gilis et al. |
| 5,807,579 | A | * | 9/1998 | Vilkov et al. |
| 6,039,974 | A |   | 3/2000 | MacLaren et al. |
| 6,103,735 | A |   | 8/2000 | Aslanian et al. |
| 6,267,986 | B1 |  | 7/2001 | Jain et al. |
| 2003/0049319 | A1 | | 3/2003 | Sriwongjanya et al. |

FOREIGN PATENT DOCUMENTS

| CA | 2054752 |   | 12/1996 |
| CN | 1089471 |   | 5/1998 |
| EP | 0 311 067 A1 |   | 4/1989 |
| EP | 0 903 151 A1 |   | 9/1997 |
| WO | WO 94/09761 A1 |   | 5/1994 |
| WO | WO 99/09957 A1 |   | 3/1999 |
| WO | WO 99/32125 | * | 7/1999 |
| WO | WO 99/32125 A1 |   | 7/1999 |

OTHER PUBLICATIONS

Lipworth, B. J., "Leukotriene-receptor antagonists"; Lancet; 1999; 353; pp. 57-62.
Diamant, Z. et al; "Anti-leukotriene therapy in asthma1"; Netherlands Journal of Medicine 1998; 53, pp. 176-189.
Choi, H-G, et al; "Development of Terfenadine-Pseudoephedrine Double-Layer Tablet Dissolution-Equivalent to Core Tablet"; Drug Development and Industrial Pharmacy; 2000; 26(6); pp. 605-611.
Chemical Abstract: Choi-H-G; "Comparative dissolution test of terfenadine-pseudoephedrine HCl double-layered and core tablet"; Yakche Hakhoechi; 1997; 27(3) pp. 213-217.
"Zafirlukast"; Martindale—The Complete Drug Reference, 33rd ed., 2002, pp. 785-786.
Leslie Hendeles, "Selecting a Decongestant" Pharmacotherapy 1993; 13(6 PT 2): 129S-134S.
Hernandez, Colin D., "Assesment of the clinical efficacy and safety of epinastine plus pseudoephedrine vs loratadine plus pserdoephedrine in perennial allergic rhinitis" National Library of Medicine, Rev Alerg Mex. Jan.-Feb. 2004; 51(1):23-8.
China Pharmacy, vol. 10, No. 3, 1999, p. 140, with translation.
WPIDS Abstract: WO 9409761 (The Thomson Corp on STN), 1995.
WPIDS Abstract: WO 9409761 (ACS on STN), 1994.

* cited by examiner

Primary Examiner—Thurman K. Page
Assistant Examiner—Humera N. Sheikh
(74) Attorney, Agent, or Firm—Michael Morris; Anthony P. Bottino; Andrea D. Small

(57) ABSTRACT

The present invention relates to novel oral pharmaceutical compositions comprising as pharmaceutically active compounds a combination of an antihistaminic-effective amount of epinastine or a pharmaceutically acceptable salt thereof and of a decongestant-effective amount of pseudoephedrine or a pharmaceutically acceptable salt thereof and further comprising suitable pharmaceutically acceptable carriers or excipients. The invention further relates to methods for the preparation these compositions and methods of using them in the treatment of allergic diseases and/or disorders.

7 Claims, No Drawings

PHARMACEUTICAL COMPOSITIONS CONTAINING EPINASTINE AND PSEUDOEPHEDRINE

RELATED APPLICATIONS

This application is a continuation of U.S. Ser. No. 09/971,870, filed on Oct. 5, 2001, now abandoned which claims benefit of U.S. Provisional Application Ser. No. 60/252,761, filed on Nov. 22, 2000, and said applications are incorporated herein by reference.

FIELD OF THE INVENTION

The present invention relates to novel oral pharmaceutical compositions comprising as pharmaceutically active compounds a combination of an antihistaminic-effective amount of epinastine or a pharmaceutically acceptable salt thereof and of a decongestant-effective amount of pseudoephedrine or a pharmaceutically acceptable salt thereof and further comprising suitable pharmaceutically acceptable carriers or excipients. The invention further relates to methods for the preparation these compositions and methods of using them in the treatment of allergic diseases and/or disorders.

DETAILED DESCRIPTION OF THE INVENTION

The present invention provides for novel oral pharmaceutical compositions comprising as pharmaceutically active compounds a combination of an antihistaminic-effective amount of epinastine or a pharmaceutically acceptable salt thereof and of a decongestant-effective amount of pseudoephedrine or a pharmaceutically acceptable salt thereof and further comprising pharmaceutically acceptable carriers or excipients under the proviso that the composition does not contain a leukotriene antagonist.

As an additional active compound the compositions according to the invention may optionally contain one or several compounds selected from the group consisting of mucolitic and analgesic-antipyretic compounds and vitamines. Preferred mucolitic ingredients are selected from bromhexine and ambroxol. Preferred analgesic-antipyretic compounds are selected from paracetamol and obuprofen. Preferred vitamines are selected from vitamine B2, B6 and C.

The pharmaceutical compositions according to the invention are useful for the treatment of allergic rhinitis, allergic congestion of the Eustachian tubes and/or other diseases from allergic origin deserving the administration of antihistamine and decongestant drugs. Furthermore the compositions according to the invention are useful in the treatment of for instance common cold and in the symptomatic relief associated with cough, cold and flu symptoms. The use of the pharmaceutical compositions according to the invention for the treatment of allergic rhinitis, allergic congestion of the Eustachian tubes and/or other diseases from allergic origin deserving the administration of antihistamine and decongestant drugs is preferred.

In a preferred embodiment the pharmaceutical composition according to the invention contains as the active ingredients only an antihistaminic-effective amount of epinastine or a pharmaceutically acceptable salt thereof and a decongestant-effective amount of pseudoephedrine or a pharmaceutically accptable salt thereof In a preferred embodiment the present invention relates to an oral pharmaceutical composition, preferably a bilayer tablet, providing for a sustained release of the decongestant effective amount of pseudoephedrine and an immediate release of an antihistaminic effective amount of epinastine.

Particularly preferred according to the invention is a bilayer tablet wherein a first layer A, providing for the sustained release of pseudoephedrine, comprises a decongestant effective amount of pseudoephedrine or a pharmaceutically acceptable salt thereof and wherein a second layer B, providing for the immediate release of epinastine, comprises an antihistaminic effective amount of epinastine or a pharmaceutically acceptable salt thereof. The bilayer tablet according to the invention may additionally contain a tablet coating C consisting of pharmaceutically acceptable excipients which mask the bitter taste of one of the active compounds.

In a preferred embodiment of the invention layer A of the bilayer tablet according to the invention comprises a decongestant effective amount of pseudoephedrine or a pharmaceutically acceptable salt thereof in a matrix of a swellable hydrophilic polymer which provides a sustained release profile in a period of 3 to 24, preferably 6 to 18, most preferably about 12 hours.

According to the invention the term pharmaceutically acceptable salts stands for acid addition salts of the active compounds pseudoephedrine and epinastine. These acid addition salts can be formed with anorganic acids like hydrochloric acid, hydrobromic acid or sulfuric acid or with organic acids as for instance oxalic acid, fumaric acid or methansulfonic acid. Epinastine is preferably used as its hydrochloric acid addition salt. Pseudoephedrine is preferably used as the hydrochloride or the sulfate. Within the present invention pseudoephedrine sulfate is most preferred.

The release of pseudoephedrine takes place over 3 to 24, preferably 6 to 18, most preferably about 12 hours. This bilayer tablet is designed to be preferably administered twice daily.

The concentration range of pseudoephedrine salt in the compositions according to the invention is between 5 and 240 mg/tablet, preferably 10 to 200 mg/tablet, more preferably 60 to 180 mg/tablet, preferably 80 to 140 mg/tablet, most preferably 120 mg/tablet. The concentration range of epinastine salt in the compositions according to the invention is between 2 and 20 mg/tablet, preferably 5 to 10 mg/tablet, more preferably 10 mg/tablet.

Each layer of the tablet is in contact with each other in a portion of their surface, but provides independent release profiles for both active substances mentioned before. The sustained release layer A consists of pseudoephedrine or a pharmaceutically acceptable salt thereof and a swellable hydrophilic polymer.

Typical swellable hydrophilic polymers include cellulosic ethers such as methylcellulose, hydroxypropylcellulose, hydroxypropylmethylcellulose, hydroxymethylcellulose, hydroxyethylcellulose, carboxymethylcellulose and carboxyethylcellulose or mixtures thereof. The use of hydroxypropylmethylcellulose (HPMC) is preferred. Particularly useful are the HPMC polymers HPMC USP2910 and USP2208 like for instance Methocel E5, E4M, E15M, K15M, and K100M supplied by the Dow Chemical Company. In the aformentioned abbreviations the designation "E" refers to USP2910 whereas "K" refers to USP2208. The number designation refers to the viscosity in a 2% aqueous solution (e.g. 5 designates a viscosity of 5 cps; 15M designates a viscosity of 15000 cps).

The excipients that could be optionally used in the sustained release layer A are insoluble polymers, soluble or insoluble fillers, antiadherents, coloring agents, lubricants and additional binders. Typical fillers are for example lactose, microcrystalline cellulose, dibasic calcium phosphate and cornstarch. Examples of antiadherents, which are used to prevent tablets from sticking to the tablet press, are colloidal silicon dioxide and talc. Magnesium stearate, talc and stearic acid are typical lubricants. Typical binders are povidone, and cornstarch.

The immediate release matrix layer B comprises epinastine within different combinations of excipients. The excipients that could be optionally used in the immediate release layer B are insoluble polymers, soluble or insoluble fillers, antiadherents, lubricants, coloring agents, disintegrants and additional binders. Typical fillers are for example lactose, microcrystalline cellulose, dibasic calcium phosphate and cornstarch. Examples of antiadherents, which are used to prevent tablets from sticking to the tablet press, are colloidal silicon dioxide and talc. Typical disintegrants are crospovidone, sodium starch glycolate and crosscarmellose sodium. Typical coloring agents are selected from FD&C red 40 HT Aluminum lake, 2-hydroxy-1,1'-azonaphthalene-3,6,4'-trisulfonic acid trisodium salt, erythrosine, iron oxides, 1-(4-sulpho-1-naphthylazo)-2-naphthol-6,8-disulphonic acid trisodium salt, 2',4',5',7'-tetrabromo-4,5,6,7-tetrachloro-fluorescein disodium salt, 2,4,5,7-Tetraiodo-3,6-dihydroxyxanthene-9-spiro-1'-(4',5',6',7'-tetrachloro-3'H-isobenzofuran-3'one dipotassium salt, trisodium 3-carboxy-5-hydroxy-1-p-sulphophenyl-4-p-sulfophenylazopyrazole, 6-hydroxy-5-((4-sulphonphenyl)azo-2-naphthalenesulphonic acid disodium salt and optionally aluminium lakes thereof. Magnesium stearate, talc and stearic acid are typical lubricants. Typical binders are povidone, and cornstarch.

Water and ethanol are examples of volatile components which can be used in the manufacture process of both layers to granulate powders. These volatile components are removed during processing and therefore do not appear in the finished product.

The tablet coating is optional since the presence of it does not modify significantly the release rates of the active substances present in the core layers. The presence of the coating is preferred because it masks the bitter taste of one of the active substances and enhances the properties of dosage form. Because of that a lot different coatings with different polymers, and plasticizers and other excipients could be used with the condition of not modifying significantly the release profile of the active substances present in the core tablet. A typical coating comprises a polymer such as hydroxypropylmethylcellulose and a plasticizer such as polyethylene glycol. Optional excipients could be added to the coating like antifoaming agents and opacifying. Example of an antifoaming agent is silicone. Examples of opacifying agents are titanium dioxide, talc and aluminum lake dyes.

The invention will be further described by the following examples. These examples disclose certain preferred embodiments of the invention. The methods of manufacturing the compositions according to the invention like for instance granulation, tablet compression, tablet coating etc. are well known to the person skilled in the art. Those skilled in the art will appreciate that various changes, modifications and substitutions can be made therein without departing from the spirit of the invention. Accordingly, it is intended that the invention be not limited to the following explicitly disclosed examples.

EXAMPLE NO 1

| Composition | |
|---|---|
| Core A. First layer | |
| Layer pseudoephedrine | mg/tablet |
| Pseudoephedrine sulfate | 120.00 |
| Methocel K 15 M PRCR* | 198.00 |
| Lactose Monohydrate | 105.10 |
| Microcrystalline cellulose | 106.00 |
| Colloidal silicon dioxide | 1.65 |
| Magnesium Stearate | 2.75 |
| Povidone | 16.50 |
| Total first layer | 550.00 |
| B. Second layer | |
| Layer Epinastine | mg/tablet |
| Epinastine HCl | 10.00 |
| FD&C red 40 HT Aluminum lake (allura red AC) | 0.38 |
| Microcrystalline cellulose | 70.00 |
| Lactose Monohydrate | 154.62 |
| Povidone | 12.50 |
| Magnesium Stearate | 2.50 |
| Total second layer | 250.00 |
| Total core | 800.00 |
| C. Coating | |
| Film Coating | mg/tablet |
| Methocel ES | 15.00 |
| Polyethylene Glycol 6000 | 1.97 |
| Silicone antifoam S184 | 0.03 |
| Total film coating | 17.00 |
| Total Film coated tablet | 817.00 |

*PR means Premium grade and CR means Controlled Released grade.

Method of Manufacture

A. First Layer:

A1. Dissolve povidone in a hydroalcoholic mixture;

A2. Blend pseudoephedrine sulfate, a portion of the microcrystalline cellulose, lactose and Methocel K15M for 5–30 minutes in a suitable mixer.

A3. Use alcoholic or hydroalcoholic solution prepared previously in step A1. to granulate the powder mix.

A4. Dry and mill the pseudoephedrine sulfate granulation from step A3, using suitable size screen.

A5. Blend the screened pseudoephedrine sulfate granulation with a portion of the microcrystalline cellulose and colloidal silicon dioxide for 3–15 minutes.

A6. Add magnesium stearate and blend for 3–15 minutes.

B Second Layer:

B1. Pass through a suitable screen Epinastine HCL, Allura red AC (FD & C red 40 HT) aluminum lake and microcrystalline cellulose. Blend for 5–30 minutes in a suitable mixer.

B2. Add lactose and povidone. Blend for 60 minutes 15–120 minutes in a suitable mixer.

B3. Add magnesium stearate. Blend for 3–20 minutes in a suitable mixer.

C. Compression:

Compress A and B into a suitable bilayer tableting machine in suitable size tablets.

D. Coating

D1. Dissolve Methocel E5 and Polyethylene Glycol in suitable amount of water.

D2. Dissolve silicone antifoam in suitable amount of isopropilic alcohol.

D3. Add 2. to 1. and mix.

D4. Coat tablets with the Methocel E5/Polyethylene glycol solution from step D3. in a suitable coater.

EXAMPLE NO 2

Composition

Core
A. First layer

| Layer pseudoephedrine | Mg/tablet |
| --- | --- |
| Pseudoephedrine sulfate | 120.00 |
| Methocel K 15 M PRCR* | 198.00 |
| Lactose Monohydrate | 126.50 |
| Microcrystalline cellulose | 100.00 |
| Colloidal silicon dioxide | 2.75 |
| Magnesium Stearate | 2.75 |
| Total first layer | 550.00 |

B. Second layer

| Layer Epinastine | Mg/tablet |
| --- | --- |
| Epinastine HCl | 10.00 |
| Lactose Monohydrate | 168.40 |
| Microcrystalline cellulose | 70.00 |
| Punceau 4R red aluminum lake | 0.38 |
| Magnesium Stearate | 1.25 |
| Total second layer | 250.00 |
| Total core | 800.00 |

C. Coating

| Film Coating | mg/tablet |
| --- | --- |
| Methocel ES | 4.42 |
| Polyethylene Glycol 6000 | 2.72 |
| Talc | 8.76 |
| Titanium dioxide | 1.10 |
| Total film coating | 17.00 |
| Total Film coated tablet | 817.00 |

*PR means Premium grade and CR means Controlled Released grade.

Method of Manufacture

First Layer:

A1. Blend pseudoephedrine sulfate, microcrystalline cellulose, lactose, colloidal silicon dioxide and HPMC K15M for 5–30 minutes in a suitable mixer.

A2. Add magnesium stearate and blend for 3–15 minutes.

B. Second Layer:

B1. Pass through a suitable screen Epinastine HCl, and microcrystalline cellulose. Blend for 5–30 minutes in a suitable mixer.

B2. Add lactose. Blend for 60 minutes 15–120 minutes in a suitable mixer.

B3. Add magnesium stearate. Blend for 3–20 minutes in a suitable mixer.

C. Compression:

Compress A and B into a suitable bilayer tableting machine in suitable size tablets.

D. Coating

D1. Dissolve Methocel E5 and Polyethylene Glycol in suitable amount of water.

D2. Add Titanium Dioxide and Talc in suitable amount of water and mix

D3. Add 2. to 1. And mix.

D4. Coat tablets with the Methocel E5/Polyethylene glycol solution from step D3. in a suitable coater.

EXAMPLE NO 3

Core
A. First layer

| Layer pseudoephedrine | Mg/tablet |
| --- | --- |
| Pseudoephedrine sulfate | 120.00 |
| Methocel K4M PRCR | 247.50 |
| Lactose Monohydrate | 166.00 |
| Talc | 11.00 |
| Magnesium Stearate | 5.50 |
| Total first layer | 550.00 |

*PR means Premium grade and CR means Controlled Released grade.

Second layer and coating are identical to example 2; the manufacture method was conducted analogously to the method outlined in example 2;

EXAMPLE NO 4

Core
A. First layer

| Layer pseudoephedrine | Mg/tablet |
| --- | --- |
| Pseudoephedrine sulfate | 120.00 |
| Methocel K15 M PRCR | 198.00 |
| Lactose Monohydrate | 99.50 |
| Microcrystalline cellulose | 99.50 |
| Colloidal silicon dioxide | 2.75 |
| Povidone | 27.50 |
| Magnesium stearate | 2.75 |
| Total | 550.00 |

*PR means Premium grade and CR means Controlled Released grade.

Second layer and coating are identical to example 1; the manufacture method was conducted analogously to the method outlined in example 1;

EXAMPLE NO 5

Core
A. First layer

| Layer pseudoephedrine | Mg/tablet |
| --- | --- |
| Pseudoephedrine sulfate | 120.00 |
| Methocel K15M CR | 330.00 |
| Lactose | 83.50 |
| Talc | 11.00 |
| Magnesium Stearate | 5.50 |
| Total | 550.00 |

*CR means Controlled Released grade.

Second layer and coating are identical to example 1; the manufacture method was conducted analogously to the method outlined in example 1;

EXAMPLE NO 6

| Core<br>A. First layer | |
|---|---|
| Layer pseudoephedrine | Mg/tablet |
| Pseudoephedrine sulfate | 120.00 |
| Methocel K15M CR | 275.00 |
| Microcrystalline Cellulose | 138.50 |
| Talc | 11.00 |
| Magnesium Stearate | 5.50 |
| Ethanol | sq. |
| Total | 550.00 |

*CR means Controlled Released grade.

Second layer and coating are identical to example 1; the manufacture method was conducted analogously to the method outlined in example 1;

EXAMPLE NO 7

| Core<br>A. First layer | |
|---|---|
| Layer pseudoephedrine | Mg/tablet |
| Pseudoephedrine sulfate | 120.00 |
| Methocel K15M CR | 215.00 |
| Dibasic Calcium phosphate | 108.50 |
| Ethylcelullose | 40.00 |
| Talc | 11.00 |
| Magnesium Stearate | 5.50 |
| Ethanol | s.q. |
| Total | 500.00 |

*CR means Controlled Released grade.

Second layer and coating are identical to example 1; the manufacture method was conducted analogously to the method outlined in example 1;

EXAMPLE NO 8

| Core<br>A. First layer | |
|---|---|
| Layer pseudoephedrine | Mg/tablet |
| Pseudoephedrine sulfate | 120.00 |
| Methocel K15M CR | 137.50 |
| Methocel K100M CR | 137.50 |
| Lactose | 138.50 |
| Talc | 11.00 |
| Magnesium Stearate | 5.50 |
| Ethanol | s.q. |
| Total | 550.00 |

*CR means Controlled Released grade.

Second layer and coating are identical to example 1; the manufacture method was conducted analogously to the method outlined in example 1;

EXAMPLE NO 9

| Core<br>A. First layer | |
|---|---|
| Layer pseudoephedrine | Mg/tablet |
| Pseudoephedrine sulfate | 120.00 |
| Methocel K100M CR | 275.00 |
| Lactose | 138.50 |

EXAMPLE NO 9-continued

| Core<br>A. First layer | |
|---|---|
| Layer pseudoephedrine | Mg/tablet |
| Talc | 11.00 |
| Magnesium Stearate | 5.50 |
| Ethanol | s.q. |
| Total | 550.00 |

*CR means Controlled Released grade.

Second layer and coating are identical to example 1; the manufacture method was conducted analogously to the method outlined in example 1;

EXAMPLE NO 10

| Core<br>A. First layer | |
|---|---|
| Layer pseudoephedrine | Mg/tablet |
| Pseudoephedrine sulfate | 120.00 |
| Methocel K15M CR | 206.20 |
| Methocel K100M CR | 68.80 |
| Lactose | 138.50 |
| Talc | 11.00 |
| Magnesium Stearate | 5.50 |
| Ethanol | s.q. |
| Total | 550.00 |

*CR means Controlled Released grade.

Second layer and coating are identical to example 1; the manufacture method was conducted analogously to the method outlined in example 1;

EXAMPLE NO 11

| Core<br>A. First layer | |
|---|---|
| Layer pseudoephedrine | Mg/tablet |
| Pseudoephedrine sulfate | 120.00 |
| Methocel K15M CR | 235.00 |
| Dibasic Calcium phosphate | 108.50 |
| Ethylcellulose | 20.00 |
| Talc | 11.00 |
| Magnesium Stearate | 5.50 |
| Ethanol | s.q. |
| Total | 500.00 |

*CR means Controlled Released grade.

Second layer and coating are identical to example 1; the manufacture method was conducted analogously to the method outlined in example 1;

EXAMPLE NO 12

| Core<br>A. First layer | |
|---|---|
| Layer pseudoephedrine | Mg/tablet |
| Pseudoephedrine sulfate | 120.00 |
| Methocel K15M CR | 255.00 |
| Lactose | 40.00 |
| Microcrystalline Cellulose | 68.50 |
| Talc | 11.00 |
| Magnesium Stearate | 5.50 |

EXAMPLE NO 12-continued

Core
A. First layer

| Layer pseudoephedrine | Mg/tablet |
|---|---|
| Ethanol | s.q. |
| Total | 500.00 |

*CR means Controlled Released grade.

Second layer and coating are identical to example 1; the manufacture method was conducted analogously to the method outlined in example 1;

EXAMPLE NO 13

Core
A. First layer

| Layer pseudoephedrine | Mg/tablet |
|---|---|
| Pseudoephedrine sulfate | 120.00 |
| Methocel K15M CR | 255.00 |
| Dibasic calcium phosphate | 108.50 |
| Talc | 11.00 |
| Magnesium Stearate | 5.50 |
| Ethanol | s.q. |
| Total | 500.00 |

*CR means Controlled Released grade.

Second layer and coating are identical to example 1; the manufacture method was conducted analogously to the method outlined in example 1;

The invention claimed is:

1. A bilayer tablet consisting of a combination of an antihistaminic-effective amount of epinastine or a pharmaceutically acceptable salt thereof and a decongestant-effective amount of pseudoephedrine or a pharmaceutically acceptable salt thereof and additional pharmaceutically acceptable carriers or excipients and may additionally contain a tablet coating C consisting of pharmaceutically acceptable excipients, with the proviso that the composition does not contain a leukotriene antagonist, wherein a first layer A, providing for the sustained release of pseudoephedrine, comprises a decongestant-effective amount of pseudoephedrine or a pharmaceutically acceptable salt thereof in a matrix of a swellable hydrophilic polymer and wherein a second layer B, providing for the immediate release of epinastine, comprises an antihistaminic-effective amount of epinastine or a pharmaceutically acceptable salt thereof and wherein the epinastine layer is prepared by direct compression.

2. A bilayer tablet according to claim 1, wherein the concentration range of the pharmaceutically acceptable salt of pseudoephedrine is 5 to 240 mg/tablet and the concentration range of the pharmaceutically acceptable salt of epinastine salt is 2 to 20 mg/tablet.

3. A bilayer tablet according to claim 2, wherein layer A comprises 120 mg pseudoephedrine sulfate and layer B comprises 10 mg epinastine-HCl.

4. A bilayer tablet according to claim 1, which contains as active ingredients only the antihistaminic-effective amount of epinastine or a pharmaceutically acceptable salt thereof and the decongestant-effective amount of pseudoephedrine or a pharmaceutically acceptable salt thereof.

5. A method of treating allergic rhinitis, allergic congestion of the Eustachian tubes and/or other diseases of allergic origin treatable by the administration of antihistaminic and decongestant agents, comprising administering to a host in need of such treatment a bilayer tablet according to claim 1 or 4.

6. A method according to claim 5, wherein the condition treated is allergic rhinitis.

7. A method of treating the common cold, cough and/or symptoms associated with the common cold or flu, comprising administering to a host in need of such treatment a bilayer tablet according to claim 1 or 4.

* * * * *